United States Patent
Winsor et al.

(10) Patent No.: US 10,849,497 B2
(45) Date of Patent: Dec. 1, 2020

(54) APPARATUS AND METHOD FOR OPHTHALMIC NEURAL SCANNING

(71) Applicant: REBIScan, Inc., Boston, MA (US)

(72) Inventors: Robert Winsor, Hamilton, VA (US); Shane Pixton, Broad Run, VA (US); James Esser, Ashburn, VA (US)

(73) Assignee: REBISCAN, INC., Boston, MA (US)

( * ) Notice: Subject to any disclaimer, the term of this patent is extended or adjusted under 35 U.S.C. 154(b) by 70 days.

(21) Appl. No.: 16/354,749

(22) Filed: Mar. 15, 2019

(65) Prior Publication Data

US 2019/0282090 A1    Sep. 19, 2019

Related U.S. Application Data

(60) Provisional application No. 62/644,371, filed on Mar. 16, 2018.

(51) Int. Cl.
  *G06K 9/00*    (2006.01)
  *A61B 3/14*    (2006.01)
  (Continued)

(52) U.S. Cl.
  CPC .............. *A61B 3/14* (2013.01); *A61B 3/0008* (2013.01); *A61B 3/0025* (2013.01); *A61B 3/0091* (2013.01); *A61B 3/112* (2013.01)

(58) Field of Classification Search
  CPC ... H04L 63/0807; H04L 67/12; H04L 67/303; H04W 12/0609; H04W 4/70; A61B 3/0008; A61B 3/0025; A61B 3/0091; A61B 3/112; A61B 3/113; G02B 27/0172; G02B 2027/0178; G02B 27/017; G02B 2027/014; G06F 3/013
  (Continued)

(56) References Cited

U.S. PATENT DOCUMENTS 6,027,216 A * 2/2000 Guyton .................. A61B 3/113
                                                351/200
6,059,773 A * 5/2000 Maloney ................ A61B 3/107
                                                351/207

(Continued)

OTHER PUBLICATIONS

International Search Report and Written Opinion cited in corresponding International Application No. PCT/US19/22479 dated Jun. 6, 2019.

*Primary Examiner* — Charlotte M Baker
(74) *Attorney, Agent, or Firm* — Amardeep S. Grewal; Reed Smith LLP

(57) ABSTRACT

An apparatus and method for ophthalmic neural scanning including a projection apparatus configured to project a projected image onto one or more retinas of one or more eyes of a subject, one or more photodetectors disposed conjugate to the one or more retinas, the one or more photodetectors being configured to capture a reflected image reflected from the one or more retinas in response to the projected image, the reflected image including information indicating fixation of the one or more eyes, and an image capture device disposed conjugate to one or more corneas of the one or more eyes of the subject and configured to capture a diagnostic image including one or more pupils of the one or more eyes when the one or more pupils are illuminated by retroreflected light from the one or more retinas in response to the projected image.

30 Claims, 10 Drawing Sheets

(51) Int. Cl.
 *A61B 3/00* (2006.01)
 *A61B 3/11* (2006.01)

(58) Field of Classification Search
 USPC ........ 382/128; 351/209, 246, 207, 212, 200; 356/2; 606/4
 See application file for complete search history.

(56) References Cited

U.S. PATENT DOCUMENTS

| | | | |
|---|---|---|---|
| 6,916,096 B2* | 7/2005 | Eberl | A61B 3/12 351/209 |
| 9,675,248 B2* | 6/2017 | Winsor | A61B 3/12 |
| 10,386,645 B2* | 8/2019 | Abou Shousha | A61B 3/0091 |
| 10,506,165 B2* | 12/2019 | Lane | G06K 9/00604 |
| 2002/0036750 A1 | 3/2002 | Eberl et al. | |
| 2002/0091323 A1 | 7/2002 | Dreher | |
| 2007/0263171 A1 | 11/2007 | Ferguson et al. | |
| 2013/0169931 A1 | 7/2013 | Lee et al. | |
| 2017/0027437 A1 | 2/2017 | Neal et al. | |

* cited by examiner

APPARATUS AND METHOD FOR OPHTHALMIC NEURAL SCANNING

RELATED APPLICATION DATA

This application claims priority to U.S. Provisional Application No. 62/644,371, filed Mar. 16, 2018, the disclosure of which is hereby incorporated by reference in its entirety.

BACKGROUND

Brain dysfunction, including injury related to traumatic brain injury ("TBI") from concussive and subconcussive head trauma, can be difficult to diagnose, as history of such an event is often incomplete and symptoms are nonspecific and overlap with a broad range of neuropsychiatric disorders. Although many patients with dysfunction make a full recovery, a significant subset does not. Individuals that experience multiple mild traumatic brain injuries ("mTBIs") are at increased risk of persistent post-injury symptoms and long-term complications, including serious sequelae, such as chronic traumatic encephalopathy ("CTE"). Simple interventions, such as removing the patient from risky environments, may prevent these complications by allowing time for the brain to heal and preventing further injury. However, intervention requires prompt and accurate identification of patients at risk.

Eye fixation measurement can be used to assess visual impairments that are frequently indicative of brain injury or trauma, in addition to vision disorders such as strabismus. However, previous methods require a high volume of image processing or a large homogenous magnetic field to determine the accuracy of fixation. Prior art devices are not able to detect precise foveal fixation due to the inability to assess retinal position.

Additionally, existing fixation assessment devices lack any mechanisms for validating fixation captured measurements and validating the conditions under which fixation measurements are captured. For example, the amount of background light in an area, the position of a subject's eyes relative to a fixation measurement device (distance from the device, direction of a measurement device, etc.), and changes in pupil size (due to fluctuations in ambient light prior to testing, conditions such as cataracts, etc.) can all affect the accuracy of fixation measurements.

Accordingly, there is a need for improvements in fixation measurement devices that allow for rapid, non-invasive, and objective evaluation of fixation and that provide mechanisms for validating captured fixation measurements and validating the conditions under which fixation measurements are captured.

DETAILED DESCRIPTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate also comprise a portion of the invention. However, because such elements do not facilitate a better understanding of the invention, a description of such elements is not provided herein.

Figure 1A:
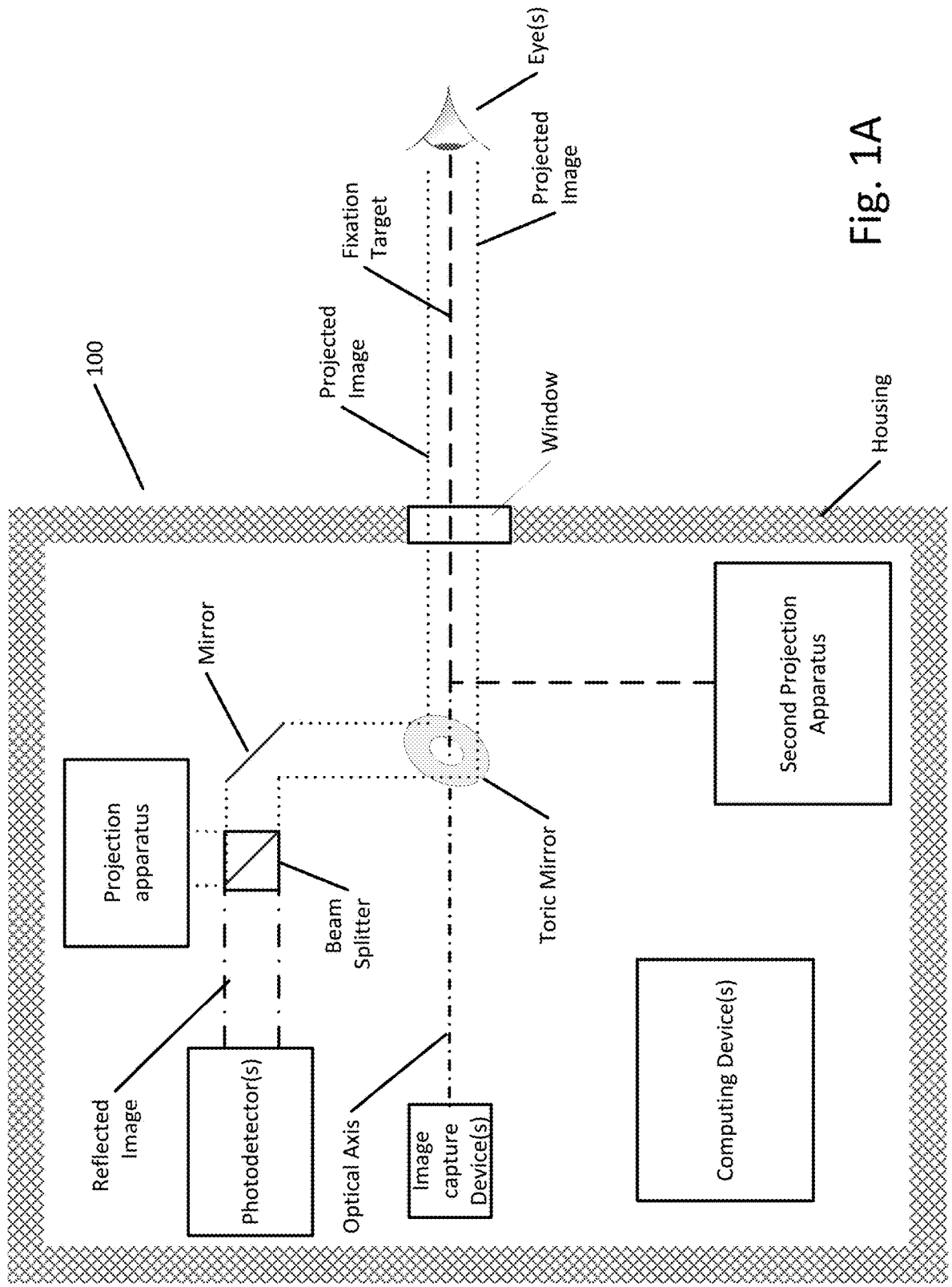
FIGS. 1A-1B illustrate ophthalmic neural scanner apparatuses according to exemplary embodiments.

FIG. 1A illustrates an ophthalmic neural scanner apparatus 100 according to an exemplary embodiment. As shown in FIG. 1A, the apparatus 100 includes a projection apparatus positioned within a housing and configured to project a projected image (shown with dotted lines) through a window of the housing and onto one or more retinas of one or more eyes of a subject. The light from the projected image enters the eyes, is imaged onto the retinas, and is then reflected off the retinas.

The projected image and the projection apparatus can take a variety of different forms. The projection apparatus can be a scan based projector with moving parts or a stationary projection apparatus with no moving parts. The projected image can be a predefined or stored image that is projected by the projection apparatus, an image that is created by components of the projection apparatus, or a stimulus that is scanned by the projection apparatus to create the appearance of a projected image to a subject. Implementations of the projection apparatus and projected image are described in greater detail below.

The projected image can be a ring image that is generated by a projection apparatus that includes a light source configured to project light and a concave toroidal mirror configured to reflect the light projected from the light source into the ring image. In this example of a stationary projection apparatus, there are no moving parts and the projected image is created from the reflection of the light from the concave toroidal mirror (which will focus the light into a ring).

The ring image can also be generated by a projection apparatus that includes a light source configured to project light through an axicon lens to generate a circular light projection and a toroidal lens configured to focus the circular light projection into the ring image.

Additionally, the ring image (or the appearance of a ring image) can also be generated by a scanning projection apparatus that includes a light source configured to project light onto a first concave mirror that is configured to rotate about a rotation axis and re-image the light projected from the light source onto a second concave mirror. Although at any given moment only a single beam of light is hitting the second concave mirror (and then the eye of the subject), the rotation by the first concave mirror occurs at high enough speeds to create the appearance of the ring image on the second concave mirror. The use of spinning mirror to generate a ring image is discussed further in U.S. Pat. No. 7,959,292 (issued Jun. 14, 2011), titled "Vision Screener," the disclosure of which is hereby incorporated by reference in its entirety. As discussed in greater detail below, the projection apparatus can also be implemented using alternative techniques and components for projecting a projected image.

The projection apparatus can also be an image projector configured to project a stimulus, such as a grid of double lines or a plurality of concentric circles. In this case, fixation can be assessed using distortions in the reflected image caused by wave-front error when the light is reflected through the structures of the eye and then detected by photodetectors.

The apparatus 100 additionally includes one or more photodetectors disposed conjugate to the one or more retinas. As used herein, the term "conjugate" refers to conjugate points of a lens system, meaning that the photodetectors are disposed at the image point corresponding to the object point of the retinas such that the retinas of the subject are imaged onto the photodetectors.

The one or more photodetectors are configured to capture a reflected image reflected from the one or more retinas in response to the projected image. As discussed in greater detail further below, the reflected image includes information indicating fixation of the one or more eyes. The photodetectors can be any suitable type of optical sensing detectors. For example, the photodetectors can be charge coupled device (CCD) sensors, complementary metal-oxide-semiconductor (CMOS) sensors, etc.

The apparatus 100 can optionally include a second projection apparatus positioned within the housing and configured to project a fixation target that is configured to appear to the subject to be centered within the projected image. The fixation target is utilized during measurements/testing to provide a visual target for a subject. For example, a subject can be directed to focus on the fixation target.

Although the fixation target appears to the eye(s) of subject to be centered within the projected image, the second projection apparatus does not necessarily have to be positioned along the optical axis of the eye. As is explained in more detail below, the apparatus can be configured such that second projection apparatus is not positioned along the optical axis of the eye but still projects a fixation target that appears to lie on the optical axis to the eyes of a subject. The second projection apparatus can include, for example, a display configured to generate the fixation target and a reflector configured to reflect the fixation target onto a window of the housing that surrounds the projection apparatus, the one or more photodetectors, and the second projection apparatus.

As shown in FIG. 1A, the apparatus 100 additionally includes a image capture device disposed conjugate to one or more corneas of the one or more eyes of the patient and configured to capture a diagnostic image including one or more pupils of the one or more eyes when the one or more pupils are illuminated by retroreflected light from the one or more retinas in response to the projected image. This process is described in more detail below.

Light from the projection apparatus enters the eye and is focused onto the retina. There is a reflected component of this light that is captured by the photodetectors and that is used to assess fixation. This type of reflection is referred to as "specular reflection." However, there is an additional type of reflection, referred to as "diffuse reflection," that causes illumination of tissue near the retina due to light scattering from the retina. This diffuse reflection of the projected light illuminates the cornea and allows for the capture of the corneal image by the image capture device.

While the pupil and the cornea are technically distinct components of the eye, the cornea resides within the eye just in front of the pupil, so that an image capture device that is disposed conjugate to (focused on) the cornea will essentially also be disposed conjugate to (focused on) the pupil. In terms of the anatomy of the eye, the cornea is the outermost layer of the eye. The pupil is created by the iris of the eye, and sits just a millimeter or two behind the cornea—there is a small gap of fluid between the two. The fluid gives the optical appearance as if the pupil is even closer to the cornea than it actually is.

Therefore, with respect to image capture devices that view the cornea or pupil from a distance of at least ⅓ meter, the terms cornea and pupil can be used interchangeably with respect to the focus area of the image capture device. In other words, if the image capture device is focused on the cornea, it is also focused on the pupil.

The image capture device can be any type of suitable digital image capture device, that uses, for example, charge-coupled device (CCD) or complementary metal-oxide-semiconductor (CMOS) technology, and can include, for example, a lens, an electronic shutter, a fixed iris, a focal plane array sensor, etc. The image capture device can have a lens on it with a focal length chosen such that both pupils can be viewed on the sensor simultaneously, while being set with fixed focus to image the pupils with best resolution. For example, two pupils spaced 75 mm apart while the image capture device is placed 400 mm from the eyes, and using a 5 mm wide sensor would require a lens with a focal length no longer than 25 mm. In practice, since patients may move around a bit during examination, a shorter focal length lens can be chosen to permit easier capture of both pupils. The image capture device can have sufficient resolution (number of pixels spanning the sensor), to get measurements of the pupil sizes of the subject with accuracy exceeding 0.1 mm. For example, a 5 megapixel digital camera with 2 um pixels and a 16 mm lens can be utilized as the image capture device and is able to achieve spatial mapping of the pupils down to 0.05 mm. The image capture device can include any combination of sensor(s) and lens(es) that effect a means of recording a facsimile of conjugate stimuli—in this case, an image of the cornea that is disposed conjugate to the image capture device.

As shown in FIG. 1A, the image capture device is aligned along the optical axis of projected image beam path and is located at the apparent position of the fixation target (the position where the fixation appears to be located to the subject). In other words, the image capture device is positioned to capture light reflected from the subject's retinas along the same path that the light traveled when entering the eyes. As used herein, the optical axis means the axis of symmetry for the light propagation path of the projected image. For example, if the projected image is a ring image than the axis of symmetry (the optical axis) would lie in the center of the ring image, co-axial with the direction of propagation of the projected image beam path. Note that when the projected image is generated by scanning (such as when using a spinning mirror), the optical axis is still the axis of symmetry of the projected image, and not each individual beam of light that makes up the projected image.

The configuration of the image capture device on the optical axis of the subject's eye and the second projection apparatus off the optical axis of the subject's eye has many technical advantages.

Light from the scanning system illuminates the facial region including one or both eyes. The light can additionally be configured to illuminate only a small area such that the majority of a subject's face other than the subject's eyes is not illuminated. When a spinning mirror is used to generate the projected image, the projected image is referred to as a "scanning image," since the projected image is created by a scanning a beam of light over a circular path. With a scanning image, each eye is able to see the appearance of a ring because the scan mirror is spinning so fast that a subject's eyes perceive it as a circle, rather than a dot being swept in the path of a circle.

The laser light entering the eyes is partially retroreflected back out of the eyes, a portion of which can be captured by a image capture device if the image capture device is sufficiently close (in angle) to the path that the light traveled when entering the eyes. In practice, this angle needs to be less than 5°, and the appearance of brightness of the pupils will increase if the angle is diminished. Therefore, the ideal location for the image capture device is at the apparent center of the circle being swept by the scanning system.

This particular location for the image capture device creates a problem, because it is at a location where a fixation target would be ideally located. To alleviate this problem, the second projection apparatus that generates the fixation target is moved to a new location. Since the image capture device is located at the center of fixation, it is ideally placed for viewing both pupils of the test subject (patient under test). Each eye, reflecting a portion of the incoming scanning light, has a pupil that appears very bright (rather than very dark as is normally otherwise the case). Due to the reflectivity of the retina, the returning light is of sufficient brightness to be among the very brightest features in a image capture device image.

In order to align the image capture device with the optical axis and simultaneously allow light retroreflected from the eyes of the subject to reach the image capture device without interfering with the projected image projection path or reflected image path, the apparatus 100 of FIG. 1A additionally includes a toric mirror aligned with the optical axis. The toric mirror is configured to reflect the projected image onto the one or more retinas and re-reflect the reflected image onto a propagation path to the one or more photodetectors. To allow light to pass through to the image capture device, the toric mirror includes an aperture configured to allow retroreflected light to pass through to the image capture device.

Figure 1B:
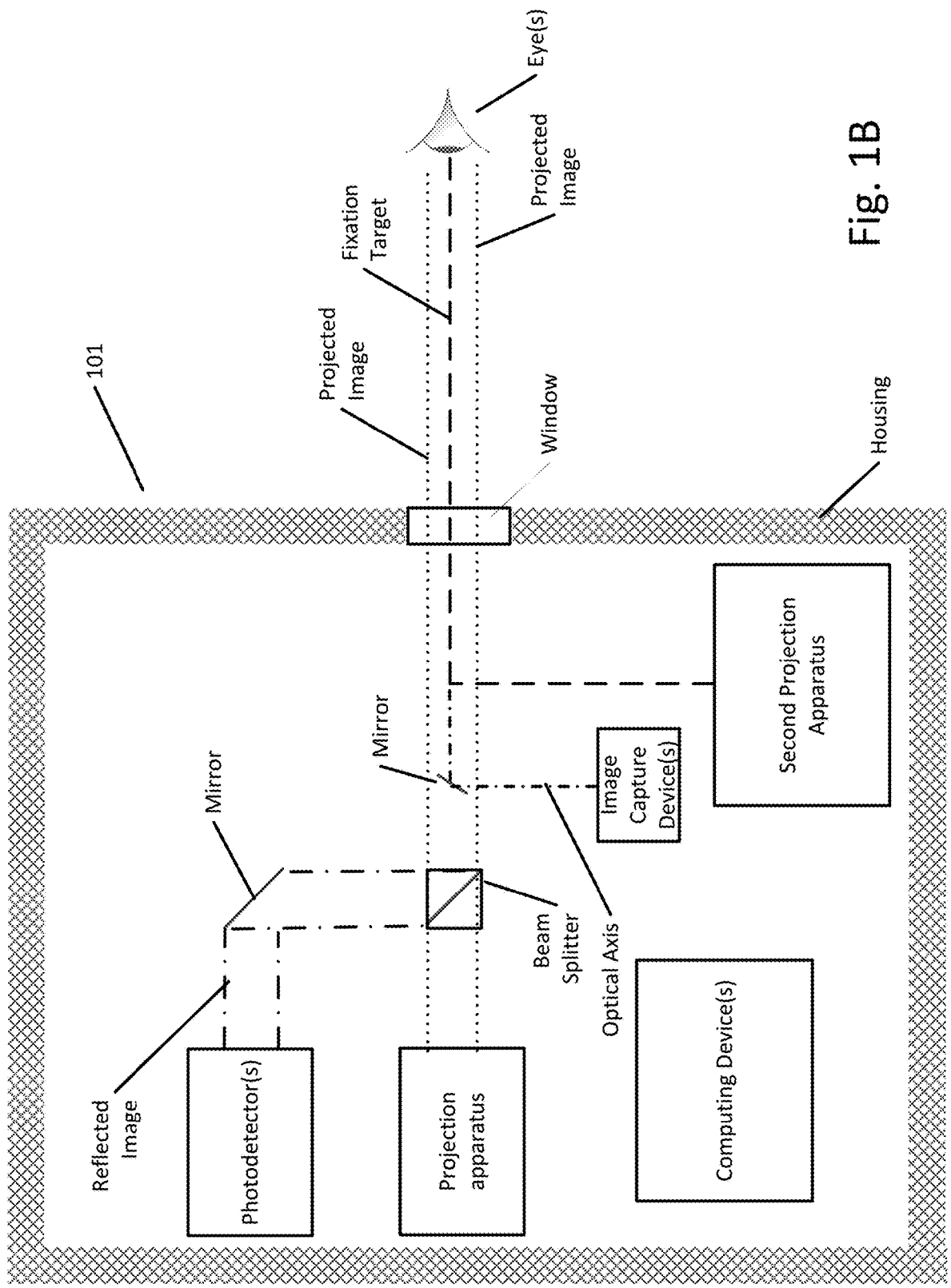

Of course, the apparatus for ophthalmic neural scanning can be implemented in alternative ways such that the toric mirror is not required. For example, FIG. 1B illustrates an apparatus 101 in which the projector generates a ring shape and a mirror is positioned within the ring to reflect retroreflected light towards a image capture device. Since the mirror is small enough to fit within the ring, there is no need for a toric mirror with an aperture. Additionally, if the image capture device is small enough to fit within the projected image being projected, the mirror could be replaced with the actual image capture device itself.

The image capture device can be used to generate and provide metadata during a fixation test. The metadata can be data pertaining to the conditions under which the fixation test is conducted (such as ambient/background light), data pertaining to attributes of the subject's eyes (such as pupil size, location, etc.), or any other information that can be extracted from the images captured by the image capture device. This functionality has many benefits. One benefit is the ability to use the image capture device to measure the amount of background light that exists in the examination room. Ideally, the test for fixation should occur in a dimly-lit setting (or a dark room), such that the pupils of the patient can dilate, which in turn produces a stronger signal for better quality measurement of fixation. If the image capture device detects a background light that is too high, the instrument can alert the user to move the test to a darker location (if possible), or the test can occur but with the metadata attached to the scan record to indicate the test was conducted in higher-than-recommended backlight room conditions. Another benefit of the image capture device is to detect when both pupils are within the regions that are ideal for the scan to occur. A user needs to move the instrument to the correct proximity to the patient (distance from patient, with correct aiming direction) for the scan to detect fixation. Since the image capture device images can be processed in near-real-time to detect whether there are pupils in the correct locations, the image capture device can automatically trigger the start of the test without the user needing to press a button.

Yet another benefit is that since the image capture device system can image the pupils and measure their sizes, it can also add this metadata to the scan data. This data may prove helpful in cases when a patient fails a test for reasons that are not completely due to fixation. For example, if a child is tested immediately after playing outdoors in bright sunlight, the pupils may not have had time to sufficiently dilate to achieve a good signal response. By including the pupil size metadata with the scan, however, this type of reason for failing a fixation test can provide a physician with a reason to re-test rather than necessarily refer the child to a costly specialist. Alternatively, a child may have a partial or full cataract as a reason for failing a fixation test, and the pupil size metadata can further assist a physician in understanding why the child was unable to achieve a good fixation measurement during the scan.

As discussed above, the fixation target projector is moved to a new location. Although the fixation target projector is moved to a new location, the fixation target is kept in the same "apparent" position using a mirror that can be part of the second projection apparatus. It can be located at the same distance from the mirror as the scanning ring (or, the original intended location of the fixation target). This mirror has a special coating applied to it that allows the infrared light of the scanning system to pass through it with high transmission value, however it reflects a significant portion of visible light from the fixation target projector, for example green light, so it permits the combination of two different sources of light to appear to be placed at the same location despite being physically located in different positions. These mirrors are, to those skilled in the art, commonly referred to as "cold mirrors" because infrared light is historically the "warm" or "hot" part of the spectrum of classical incandescent lamps. Hot mirrors, conversely, reflect the infrared and rather have high transmission of visible light. Either mirror type can be used to combine a visible light source with an infrared light source, and the use of one type of mirror over the other is not a limitation but rather a design choice.

The implementation of a cold mirror, when used in combination with an infrared scanning light for the first projector, permits the infrared scanning light, with its apparent circular shape, to appear to be surrounding the fixation target, while simultaneously appearing on the same plane as, a fixation target that is produced using visible light (for example, green light on an OLED screen).

Figure 5:
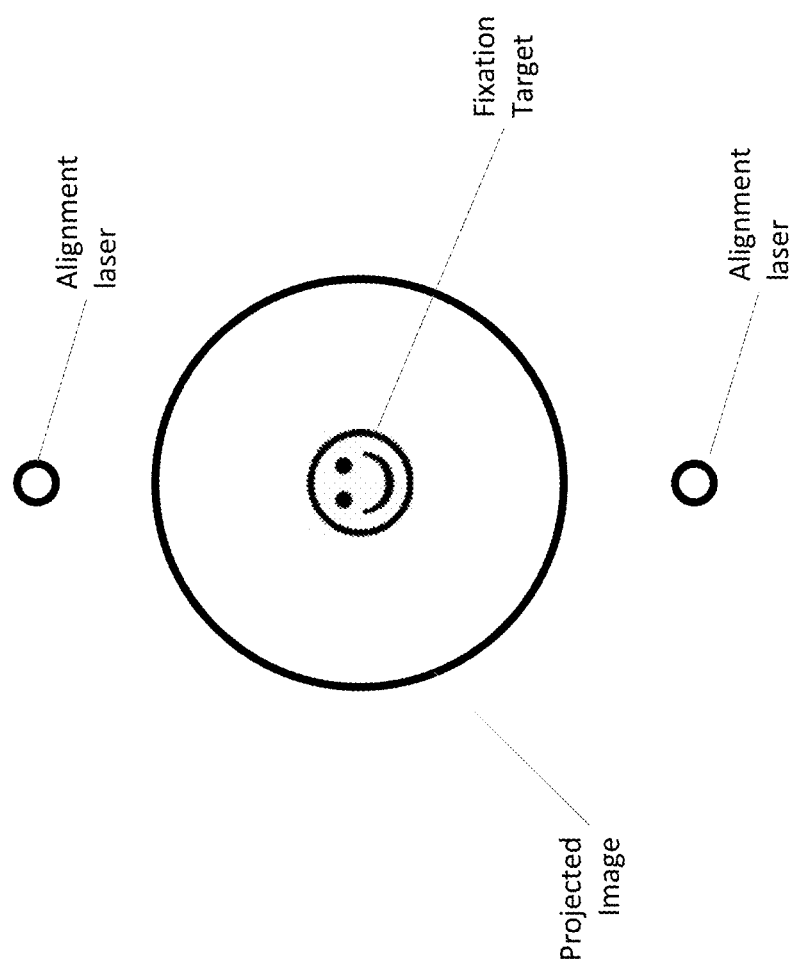
FIG. 5 illustrates the fixation target and the projected image as they would appear to a subject whose eyes are aligned with the exit pupil generated by the toric mirror.
Figure 6:
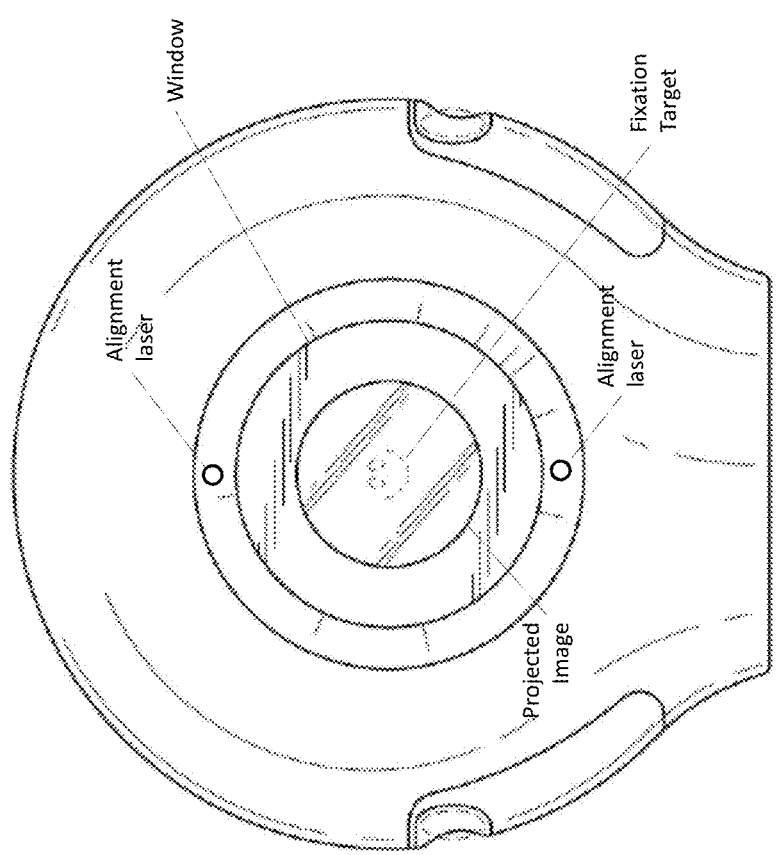
FIG. 6 illustrates a back face of the ophthalmic neural scanner according to an exemplary embodiment.

An organic light-emitting diode (OLED) screen can be used as the display of the second projection apparatus. The use of an OLED screen fixation target placed in a different location provides an additional benefit. Normally, the OLED screen is a bit large, and can be challenging to locate in such a way that the scan ring can also be viewed. By incorporating the cold mirror (or hot mirror, for alternate method), the OLED can be placed in a location where there is sufficient room for the full size display to be, apparently, superimposed onto the scan ring. The OLED display can then be used to incorporate other attention-grabbing graphics to secure the attention of a young child and draw their fixation into the central target area, thereby assisting the testing process and helping a normal healthy child to pass the test. For example, FIGS. 5-6 illustrate the reflection of a smiley face displayed on the OLED display as it would be reflected onto a window of the ophthalmic neural scanning apparatus.

The OLED display can be placed near an instrument window of the ophthalmic neural scanning apparatus, located such that it's surface is both centered and 1:1 conjugate to the projected image (such as an apparent ring swept out by the projection apparatus when using a spinning mirror).

Apparatus 100 additionally includes one or more computing devices executing specialized software routines that are used to make assessments based upon the collected data, including the reflected image and the diagnostic image. The computing devices can include processor(s) and memories operatively coupled to the processors and having instructions stored thereon that, when executed by the processors, cause the processors to perform the software routines. The software can be embodied on non-transitory computer-readable media, such as a disk, flash memory, or a hard drive.

While not shown in FIG. 1A (for clarity), the computing devices can be coupled to the other components in the apparatus 100, including the projection apparatus, the second projection apparatus, the photodetector(s), and the image capture device(s). The computing devices can be coupled via a system interconnection mechanism, such as a system bus.

The computing devices are configured to analyze the diagnostic image(s) captured by the image capture device to generate diagnostic metadata pertaining to a usage of the ophthalmic neural scanner apparatus. The diagnostic metadata can include, for example, information relating to a measurement of background light, a presence of the one or more pupils, a location of the one or more pupils, a size of the one or more pupils, and/or a blink rate of the subject.

The computing devices can additionally include a communications interface and be configured to transmit the diagnostic metadata to a display device integrated with the ophthalmic neural scanner apparatus or to transmit the diagnostic to one or more external computing devices, such as over a communication network, including wireless networks, communication cables, Bluetooth, etc. For example, the diagnostic metadata can be provided with the results of a scan in order to allow a medical professional or other operator of the apparatus to assess whether fixation measurements were captured under acceptable conditions.

The computing devices can additionally be configured to use the diagnostic metadata to control other components within the apparatus. For example, the computing devices can act as a trigger for the apparatus 100 and can determine, based upon the diagnostic metadata, when to activate the photodetectors in order to capture a reflected image. This can include determining whether the subjects pupils are present in the diagnostic image based at least in part on the diagnostic metadata, determining whether a location of the subjects pupils is within a boundary of a target location required to initiate a scan based at least in part on the diagnostic metadata, and transmitting a command to the photodetectors to capture the reflected image when the subjects pupils are present in the diagnostic image and within the boundary of the target location required to initiate a scan.

The computing devices can additionally include specialized software used to calculate fixation measurements of the eyes of the subject. As discussed in greater detail below, the fixation measurement software can utilize the projected image and the reflected image and determine fixation of the subject based on changes between the projected image and the reflected image.

The computing devices can be further configured to identify possible health conditions of the subject based on the fixation measurements and/or the diagnostic metadata. The possible health conditions include, for example brain trauma, impeded brain function, brain injury, strabismus, ocular motor apraxia, and/or amblyopia.

Additionally, the computing devices can be configured to run diagnostic routines, such as routines for assessing saccadic latency of a subject that transmit visual cues or audio cues in order to get a subject to divert their gaze and then measure the time required to achieve fixation when the subject is then directed to focus on the fixation target.

Of course, the majority of the computing devices and specialized software can also be located external to the housing. In this case, the apparatus can be include a communications interface configure to transmit obtained data and measurements to the external computing devices.

Figure 2:
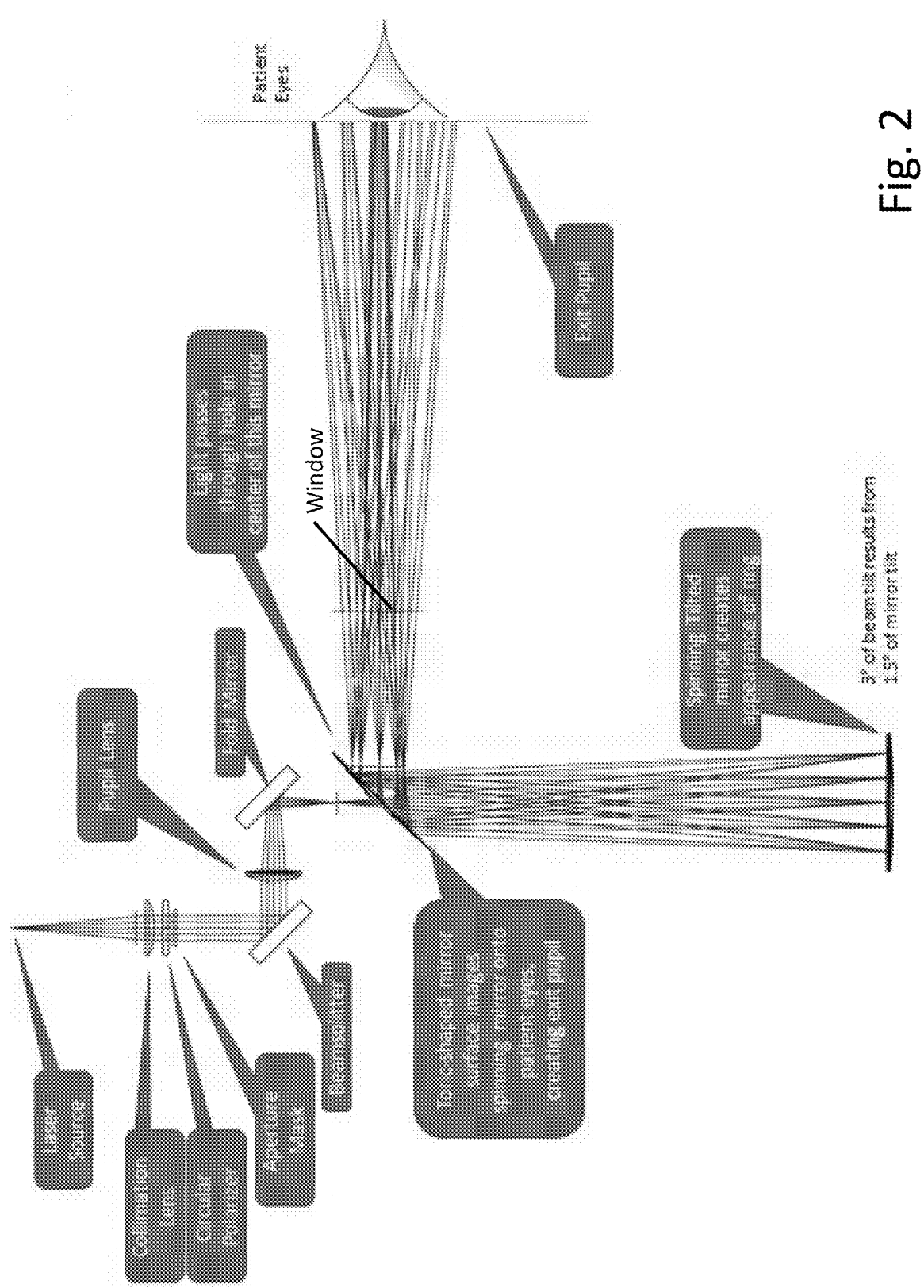
FIG. 2 illustrates an ophthalmic neural scanner apparatus including the projection apparatus according to an exemplary embodiment.

FIG. 2 illustrates an ophthalmic neural scanner apparatus including the projection apparatus according to an exemplary embodiment. FIG. 2 also illustrates the path of light from the laser source to the patient. As shown in FIG. 2, the projection apparatus includes a laser source, collimation lens, circular polarizer, aperture mask, beamsplitter, pupil lens, fold mirror, toric mirror, and spinning tilted mirror. The window of the housing (housing now shown) is also labeled for reference. Light from the laser course passes through an aperture in the toric mirror and is reflected off the spinning tilted mirror back onto the toric mirror, where it is then imaged onto the retinas of the patient/subject. The toric mirror creates an exit pupil that is aligned with the pupils of the eyes of the subject when the scan is performed. In other words, the exit pupil of the first projection apparatus, and the toric mirror, aligns with the entrance pupil of the patient. As shown in FIG. 2, the laser source and the spinning tilted mirror can correspond to the "projection apparatus" shown in the apparatus 100 of FIG. 1.

Figure 3:
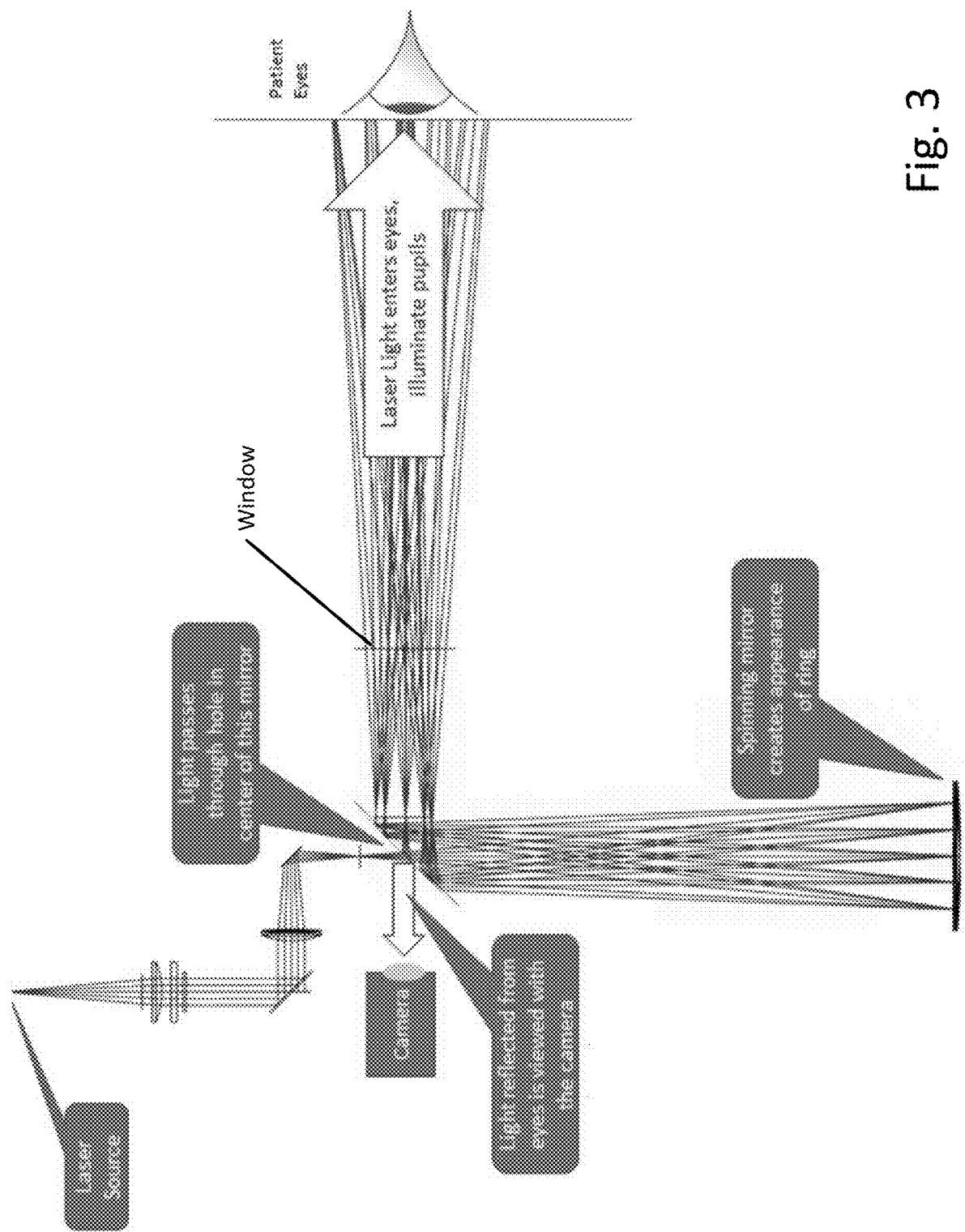
FIG. 3 illustrates the apparatus of FIG. 2, indicating the return path of light reflected from the patient's retinas.

FIG. 3 illustrates the apparatus of FIG. 2, indicating the return path of light reflected from the patient's retinas. As shown in FIG. 3, the reflected light passes through the aperture in the toric mirror and is then detected by the image capture device.

Figure 4:
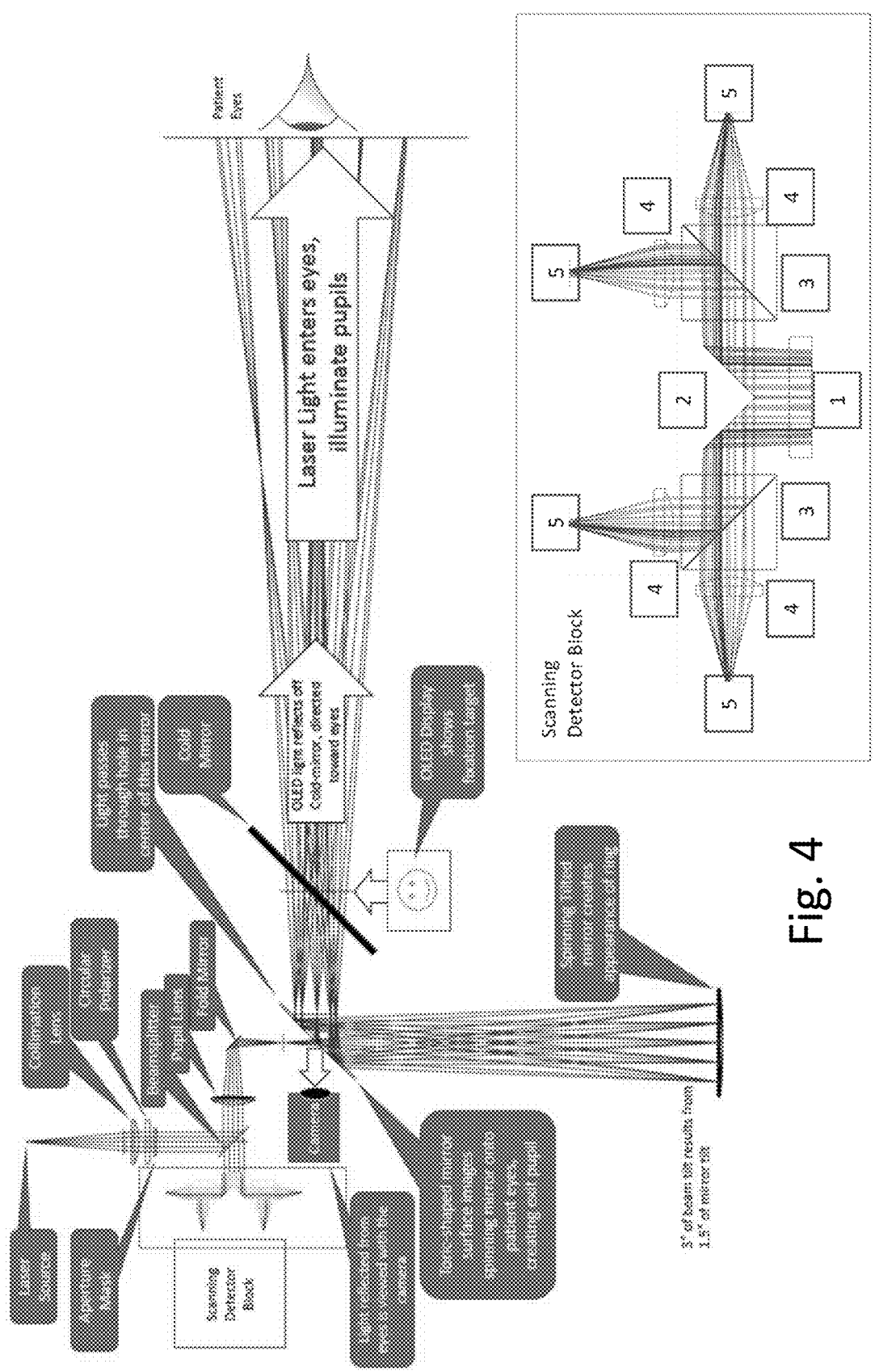
FIG. 4 illustrates an ophthalmic neural scanner apparatus including the projection apparatus, the second projection apparatus, and a camera according to an exemplary embodiment.

FIG. 4 illustrates an ophthalmic neural scanner apparatus including the first projection apparatus (producing the projected image), the second projection apparatus (producing the fixation target), and the image capture device (in this case, a camera) according to an exemplary embodiment. FIG. 4 is similar to FIGS. 2-3 but additionally includes an OLED display, as the second projection apparatus, that shows a fixation target (shown as a smiley face) and a cold mirror that reflects the fixation target toward the eyes of the subject. As discussed earlier, the fixation target will appear to the subject to be in the center of the projected image. FIG. 5 illustrates the fixation target and the projected image as they would appear to a subject whose eyes are aligned with the exit pupil generated by the toric mirror.

FIG. 4 additionally illustrates the scanning detector block in a separate box. The scanning detector block includes a bandpass optical filter (labeled "1"), a knife-edge beamsplitter ("labeled "2"), two polarizing beamsplitters (labeled "3"), four energy concentrating lens (labeled "4"), and four Photodetectors (labeled "5").

The reflected light can then be converted by the photodetectors (or a controller controlling these components) into reflected light data. The reflected light data include information indicating a fixation of the eye(s) of the subject. Fixation can be calculated, for example, based on one or more polarization-related changes between light emitted by the light source and light received from the one or more eyes of the patient, as described in U.S. patent application Ser. No. 14/806,593 (filed Jul. 22, 2015), titled "METHOD AND APPARATUS FOR FIXATION MEASUREMENT," the disclosure of which is hereby incorporated by reference in its entirety.

Fixation can additionally be determined based on polarization based changes in an image and a reflected image, as described in U.S. patent application Ser. No. 14/978,865 (filed Dec. 22, 2015), titled "APPARATUS AND METHOD FOR FIXATION MEASUREMENT WITH REFRACTION ERROR MEASUREMENT USING IMAGE SENSING DEVICES," the disclosure of which is hereby incorporated by reference in its entirety.

For example, when the image is a ring image, fixation of one or more eyes can be calculated based at least in part on one or more polarization-related changes between attributes of the scanning ring image and the reflected ring image. The ring in the reflected image can provide one of two general types of characteristics which are used to determine fixation.

For the first type, the ring image has two shorter arc regions that are dimmer than average, and two that are brighter than average. The two bright regions are roughly 180 degrees apart from each other, as are the two dim regions, with dim regions separating bright regions. This image would indicate a successful measurement of fixation. A minimum of two sequential image captures that are successful measurements of fixation can indicate the person has successfully demonstrated ability to fixate in that eye.

For the second type, a ring in the reflected image has a larger arc-length region that is bright, and there is only one such section. The ring likewise has one larger arc-length region that is dim, and there is only one. This image constitutes a failure to fixate, and indicates that scanning for fixation needs to continue.

Fixation can also be determined by measuring distortion of the image due to wave-front error, as described in U.S. Pat. No. 9,675,248 (issued on Jun. 13, 2017), titled "METHOD AND APPARATUS FOR FIXATION MEASUREMENT AND REFRACTION ERROR MEASUREMENT USING WAVE-FRONT ERROR," the disclosure of which is hereby incorporated by reference in its entirety. In this case, the image can be projected by an image projector and can include, for example, a circle or a grid in addition to the fixation target. Distortions in the reflected image can be compared with the projected image to identify fixation.

In addition to fixation measurement, the apparatus described herein can be used to determine a number of ophthalmic and brain impairments that can be based upon fixation. For example, the apparatus can be used to determine saccadic latency and brain impairments caused by brain trauma or other brain injuries, as described in U.S. patent application Ser. No. 15/472,462, titled "METHOD AND APPARATUS FOR FIXATION, ALIGNMENT, AND/OR SACCADIC MEASUREMENTS TO IDENTIFY AND/OR TRACK BRAIN FUNCTION" and filed Mar. 29, 2017, the disclosure of which is hereby incorporated by reference in its entirety.

The apparatus can be used to assess fixation differential in both eyes for the purpose of identifying a misalignment in the eyes, known as strabismus. In this case, fixation measurements for one eye can be compared with fixation for the other eye.

The apparatus can also be used to identify other potential disorders based upon fixation, such as Ambyopia or impeded brain function due to injury, fatigue, chemical involvement, or neurodegenerative disease.

FIG. 6 illustrates a back face of the ophthalmic neural scanner according to an exemplary embodiment. As shown in FIG. 6, the fixation target (smiley face) is visible in the center of the projected image, which is a ring image. Both the fixation target and the projected image are centered within a window, which can itself be circularly shaped.

FIG. 6 also illustrates alignment lasers, located above and below the projected image and the fixation target. The alignment lasers can be used as rangefinders and can be, for example, two "micro"-sized laser pointers. Each nominally 650 nm providing a ~2 mm diameter beam, ~350 mm downrange. These can be mounted to the front Bezel of the ophthalmic neural scanner, one located directly above the window and one directly below, nominally separated 75 mm. These can be internally adjusted such that they point to the center of the patient exit pupil (see section on exit pupil alignment), but with the upper laser oriented slightly right of center while the lower oriented slightly left of center such that at optimal range (400 mm from the apparent focal place of the ring), the two dots are closely spaced side-by-side, separated by 1 mm to 3 mm of distance.

Figure 7:
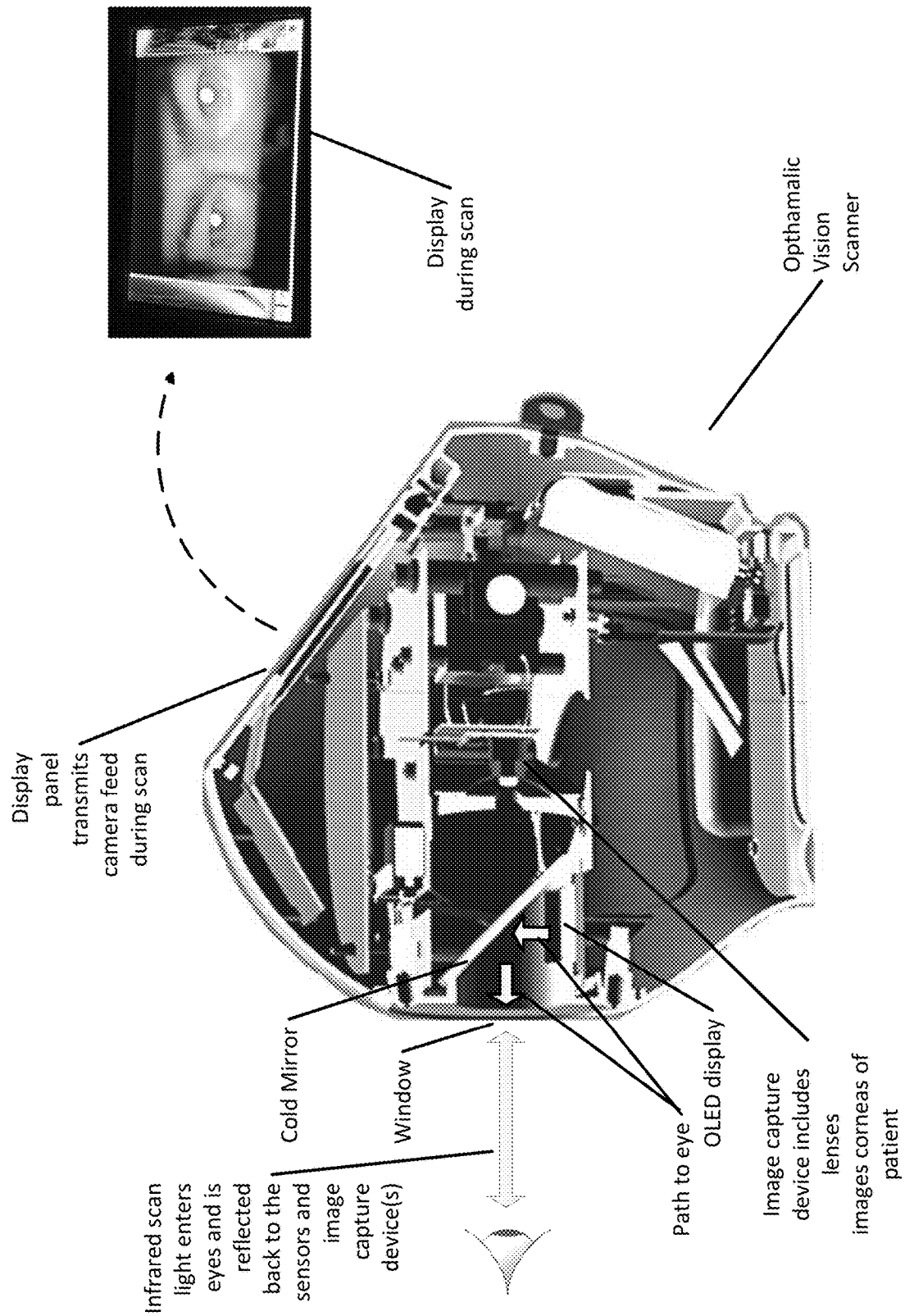
FIG. 7 illustrates the operation of the ophthalmic neural scanner shown in FIG. 6.

FIG. 7 illustrates the operation of the ophthalmic neural scanner shown in FIG. 6. As shown in FIG. 7, infrared scan light passes through a window and is imaged onto the retinas of a subject. The reflected light from the retinas then passes back through the window and to one or more photodetectors within the ophthalmic neural scanner. The retroreflected light also illuminates the cornea of the subject, allowing the image capture device to capture an image of the illuminated cornea, including the pupils of the subject. The image capture device aligned along the optical axis of the projected image that is imaged onto the patient's eyes. A display panel additionally transmits the image capture device feed during the scan.

As shown in FIG. 7, an OLED display is used to generate the fixation target, which is then reflected by a cold mirror. The circular scan pattern (infrared light) of the projected image passes through the cold mirror and the fixation target and the scanning image appear as if super-imposed upon the same visual plane. This provides the user with a fixation target and permits the image capture device to reside at the apparent physical location of the fixation target.

Figure 8:
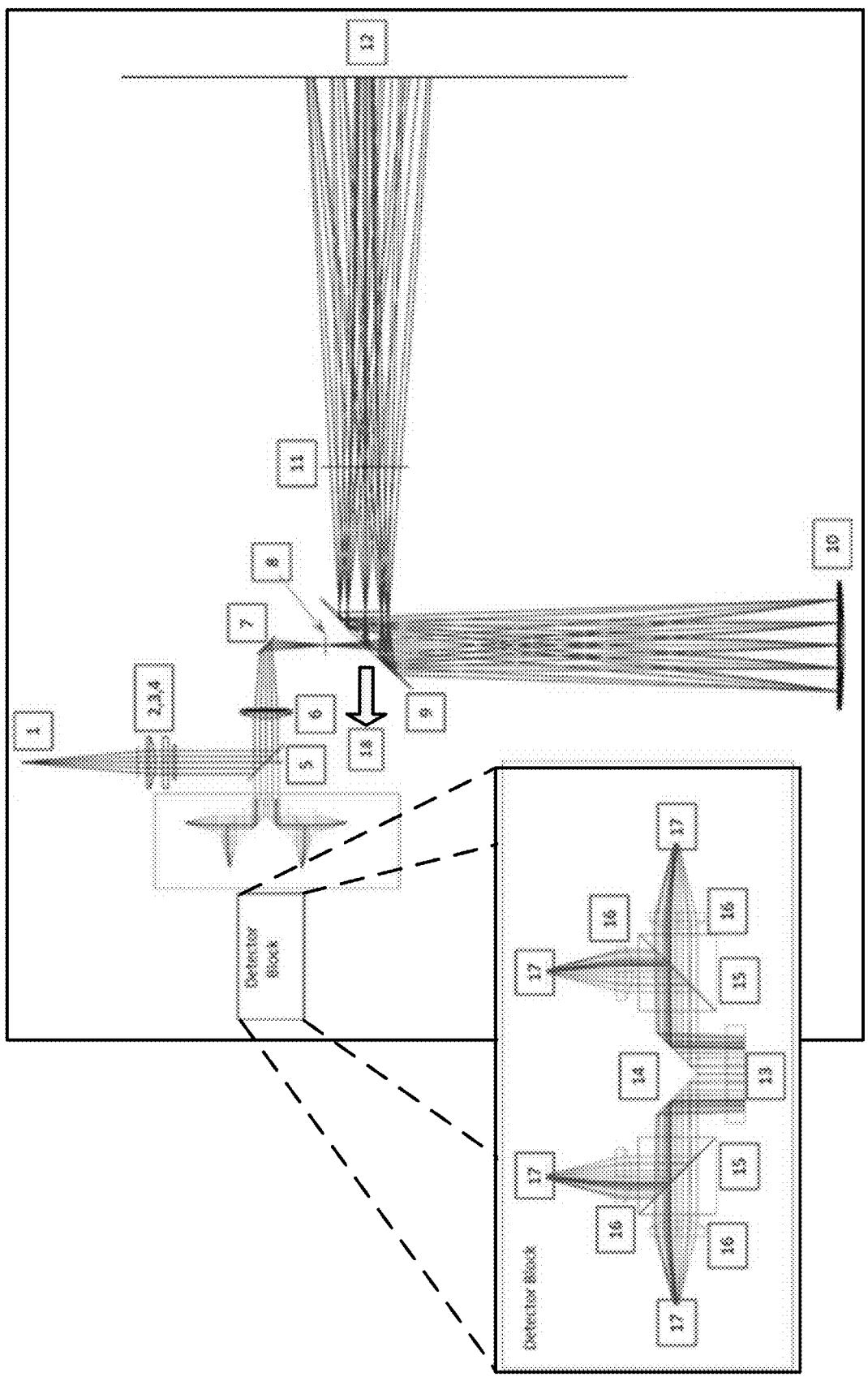
FIG. 8 illustrates a functional layout of an ophthalmic neural scanner apparatus according to an exemplary embodiment.

FIG. 8 illustrates a functional layout of an ophthalmic neural scanner apparatus according to an exemplary embodiment. The optical design of the ophthalmic neural scanner follows the functional layout as depicted in FIG. 8. It includes optical components that each perform a function, as indicated by the numerals in FIG. 8. In summary, the instrument scans a laser along the path of a 20 mm diameter ring that is located 400 mm in front of (and viewed by) the patient under test, while simultaneously capturing and measuring the amount of light reflecting off the retina of the patient's eyes. The following descriptions of each of the components utilize a local coordinate system in which the X-axis corresponds with dimensions that are conjugate to the separation between the pupils of a patient, the Z-axis corresponds to the nominal direction of the propagation of light, and the Y-axis is "left-hand" perpendicular to the X and Z axes (thumb, Y; index finger, Z; middle finger, X).

The laser source (numeral 1) can be a single-mode diode laser, wavelength 820 nm to 840 nm (nominally 830 nm), output power not to exceed 50 mW.

Laser Collimation Lens (numeral 2) can be a plano-convex lens, BK7 glass with center thickness 3.23 mm and radius of curvature of 25.84 mm. This lens is placed at a distance from the laser diode such that it will collimate the light.

Waveplate (numeral 3) can convert the highly linearly polarized output of the laser diode to circularly polarized light.

Beam Aperture (numeral 4)—the collimated beam can established by this device to have rectangular dimensions of 4.5 mm (Y) by 13 mm (X).

Beamsplitter (numeral 5) can be a 1.5 mm thick plate-type beamsplitter, 50:50 split ratio, non-polarizing, placed at a 45-deg angle to the beam Divergence lens (numeral 6) can be a plano-convex lens identical to (2) and can additionally contain anti-reflection coatings. This lens can be installed into the beam with a small tilt (nominally 3-deg, X-axis of tilt) to prevent reflections from its surfaces from entering the detector block.

Fold Mirror (numeral 7) can be a gold coated fold mirror. This fold mirror is optional for instrument function, but allows the instrument to be packaged into a compact volume.

Aperture (numeral 8) can be a 3 mm circular aperture placed at the focal point of lens (6).

Toric Mirror (numeral 9) includes a 10 mm diameter hole in the center of the mirror that the beam passes through. The hole can be drilled at a 45-deg angle to the X-axis of the substrate. A second 10 mm diameter hole can also drilled at a 45-deg angle to the X-axis of the substrate, but oriented 90 degreed from the other 10 mm hole. This lens is plano-concave, with the concave side having a toric shape. The two holes can merge at the surface such that there appears to be just one opening in the mirror at the center.

Spinning mirror (numeral 10) can be a plano-concave lens, with radius of curvature of 200 mm. Concave side can be gold coated to produce a mirror. This mirror is tilted 1.5-deg and spun about the local Z-axis to produce a 3-deg beam deviance from the input beam. The beam then travels back toward toric mirror (9) whereby the beam is deflected toward the patient.

Instrument window location (numeral 11) is the location where the window of the instrument housing can be be placed. All optical components up to this point would be housed inside a dust-tight and light-tight environment. This location should be at least 50 mm away from toric mirror (9). The angle of incidence of this window needs to be large enough to prevent a patient under test from being able to see reflections of themselves or other items in the area off this window surface. Nominally, an angle of incidence of 45 degrees is required to permit the inclusion of a secondary display for presentation to the patient under test. Note: the line depicting the location of the window in FIG. 8 is approximate only and does not represent the angle of incidence as described in this section.

Patient (numeral 12) refers to the eyes of the patient being tested. The eyes of the patient under test can be located 330 mm to 350 mm from the instrument window (11). Light will enter the eyes, be imaged onto the retinas, then reflected off the retina. Light reflected back out of the eye will follow the same path as incident light, and will continue back through optical surfaces/components (11 through 5) where upon hitting the beamsplitter (5) it will be partially separated and proceed to the detector block (13-17).

Toric mirror (9) has an aperture in the center to allow light reflected out of the eye along the optical axis of the projected image to pass through and be captured by image capture device (18). This allows the image capture device (18) to capture an image the eye of the subject as it is illuminated by the retroreflected light from the retina of the subject, including the cornea and pupil. Image capture device (18) and toric mirror (9) both lie along the optical axis of the projected image, allowing for better capture of the illumination due to retroreflected light.

Optical Filter (numeral 13) can be a bandpass filter for attenuating light that is not of interest to measure while allowing most of the light (at least 60%) at wavelengths of 830 nm to 840 nm to pass.

Knife-Edge mirror (numeral 14) can be where the separation of left and right eyes occurs. This nominally separating the beam from one size ~4.5 mm×13 mm to a size of ~4.5 mm×6.5 mm for each eye and deflecting each to a different direction 180° apart.

There are two Polarizing Beamsplitter Cubes (numeral 15) that can be optimized to split polarizations at 835 nm, sending S-polarization in a direction 90° separated from the P-polarization. There are two of these, one for each eye.

There are four Energy concentrating lens (numeral 16) that can be Plano-convex lens for concentrating the energy of the area of the beam (nominally 4.5 mm×6.5 mm) into a small area for detection with a photosensor. There are 4 of these lenses, one for each polarization of each eye.

There are four Detectors (numeral 17) that can be pre-amplified silicon photodetectors for measuring the optical signal strength of light reflected from the retinas of the eyes of the patient. There are 4 of these detectors, one for each polarization of each eye.

The apparatus can include other fold mirrors (similar to 7) at other locations of the beam and prior to surface 11. For example the long path between the toric mirror (9) and the spinning mirror (10) can include a fold mirror to allow the volume and shape of the instrument to be more ergonomic. Fold mirrors can be gold coated for >98% reflectivity and low surface scatter.

The ophthalmic neural scanner apparatus, as described in this specification and as shown in any of the preceding figures, can include a number of additional components that help to facilitate testing of the patient.

Since the ophthalmic neural scanner apparatus is an instrument with a relatively bright source of light built-in that also measures extremely dim light returning from the eyes, stray light control is very important. Accordingly, surfaces that are common to both outgoing and returning light can be configured to minimize surface scatter. Mirror surfaces can be protected gold coated (a coating process that produces minimal increase to surface scatter) and surface roughness can be configured to be 20-10 or better. Some surfaces, such as the toric mirror, can be cost prohibitive to produce with such low surface scatter, and therefore can utilize roughness that is typical of more readily available and cost effective manufacturing methods.

The housing of the ophthalmic neural scanner apparatus can be made of electrically insulating material that is lightweight (specific gravity less than 1.0), yet strong enough to handle the vibrations and use of a typical medical screening device.

The electronics and hardware of the apparatus include detectors (17), which are electrically amplified and filtered to provide good signal response at frequencies of interest (notably 100 Hz and 200 Hz, but also possibly higher harmonics). There can be four detectors, two for each eye, with each detector sampling either S-polarization or P-polarization. These detectors can be initially post-processed through a differential amplifier, in order to identify the difference in the signals between the S and P polarizations. The signals returning from the eyes are very small, and competing with significant sources of noise. To help find the frequencies of interest, a high-sample-rate digitization of the differential signal can be utilized. There can be a dedicated Analog-to-Digital Converter (ADC) operating at a sampling rate of, for example, greater than or equal to 200 kHz at 16 bits for each of the two differential detector signals. These data streams can then be sent (via any transmission means, including wireless, wired, bus, etc.) to the computing devices (which can be within the housing or external to it) for Fourier Transform processing and determination of fixation.

The ophthalmic neural scanner includes hardware and electronics that allow the apparatus to manage components and handle functions including, but not limited to: Power Supply and battery management; Lasers; Detectors; Spinning Mirror; Auxiliary optics (displays, laser rangefinder), Computing Systems, Data Collection, Differential amplification and frequency filtering, ADC: at least two channels at 200 kHz, 16-bits, Data buffering and delivery to computing system, Computing System, Central Processor, Peripheral device management, Memory management, Main user interface and Display, Control of laser on/off, motor speed, and/or OLED display stimulus.

As discussed earlier, the ophthalmic neural scanner also includes a number of software programs configured to run on various components of the apparatus and stored in memory as computer-readable instructions. The computer-readable instructions are executed on processors of the apparatus to execute the software.

For example, the device's hardware and sensors can be controlled by a single board computer. This computer can run an embedded OS, such as a version of Linux and, in addition to command and control of hardware, can run a graphical user interface program allowing users to interface with the hardware. The embedded OS provides services for local user authentication, a database server software and/or a file system for data storage, and any other open source or commercial available software to manage these services. The OS can also support drivers for WiFI and Bluetooth wireless services as well. The device can contain a capacitive touchscreen for user interaction and on which the Graphical User Interface (GUI) can be displayed. The device, upon power up, can boot directly to the GUI. The first time the device is powered on upon delivery to a customer, a setup screen can be displayed. This setup screen can allow the device to be customized to reflect the customer's use environment.

Additionally, the apparatus can include custom software programs to provide the commands and control necessary to perform the exam with the device. The software can be callable through bash or similar shell command system. The software can be compiled into specialized modules that run independently from one another. Therefore, if one module fails (other than the GUI) the user will still be able to interact with the device and troubleshoot problems. If the GUI fails, then a reboot will be required. The specialized software modules can include: hardware control, image capture device control and image processing, signal processing, data management, and/or the GUI.

A summary of these modules and their requirements are described below. Each module can communicate with other modules through the use of a message queue system based on either socket connections or interprocess communication (IPC). For example, the ZeroMQ software can be used as the basis for this communication system using IPC connections.

Hardware Control

The hardware control module is charged with the command and control of the various hardware components used in running the exam. These components include the scanning laser, motor, shutter, alignment laser, fixation target, piezo sound, IMU, and battery charger control. These devices use GPIO, I2C and SPI pins of the embedded computer for the command and control. This module can be written in the Rust language. Rust is a memory safe, low level systems programming language. The memory safe aspect of this language can be utilized to avoid memory locks or null pointers when dealing with the hardware bus communication, thereby reducing failure modes and software crashes. The module can also collect or determine status and fault messages from the hardware and provide that information to the GUI. The GUI can request hardware services through the IPC interface. These services, or functions, would include things such as opening the shutter or turning the laser on or off for example. All functions required to provide full use of the device for its intended purpose shall be available through the IPC interface. Functions required to ensure this functionality may remain internal to this module. The hardware module will be start on boot to initialize the hardware, perform status checks and self tests. The hardware module will run as a system service in Linux.

Image Capture Device Control and Image Processing

Figure 9:
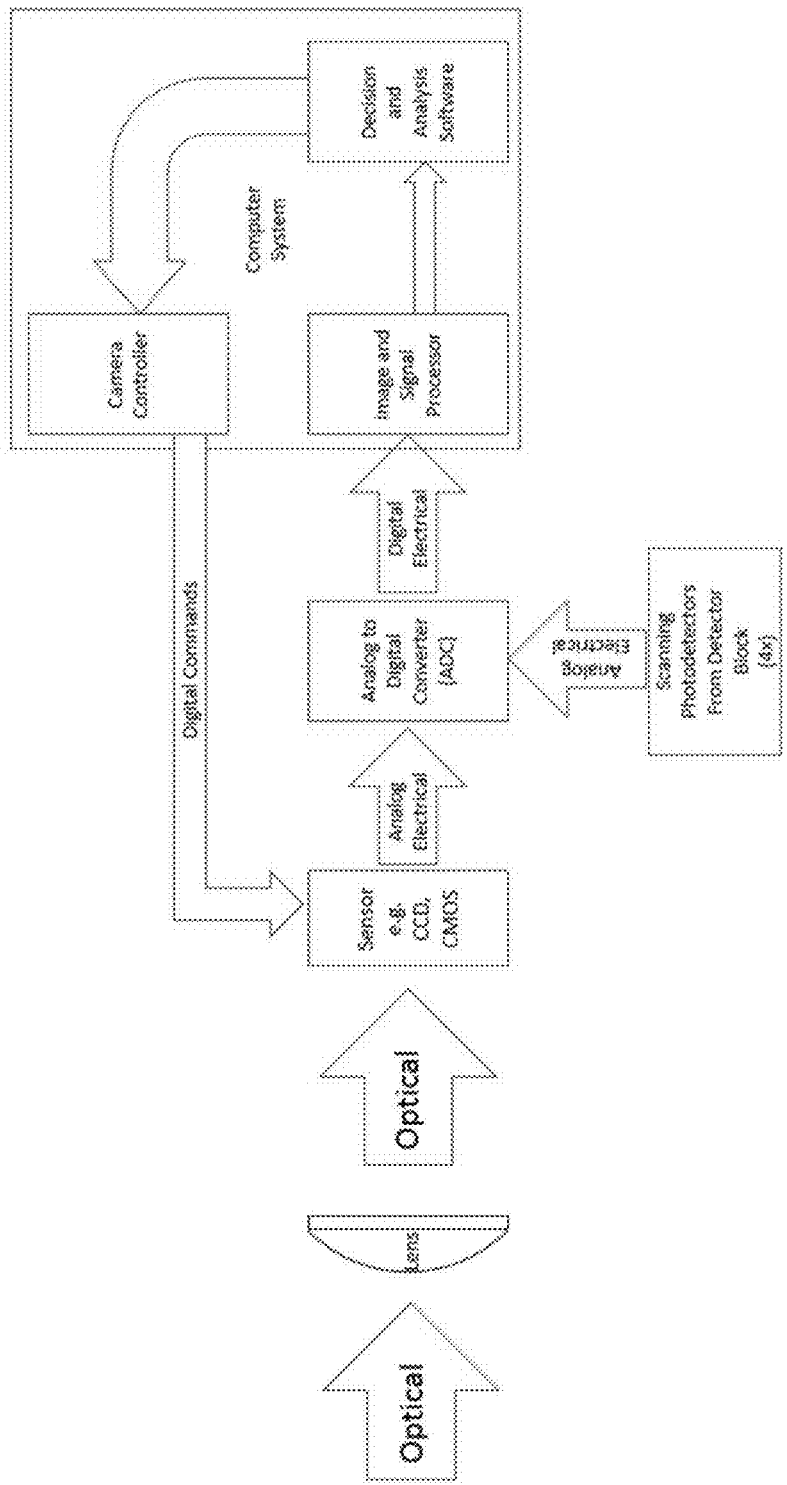
FIG. 9 illustrates components of the image capture device according to an exemplary embodiment.

FIG. 9 illustrates components of the image capture device (in this case, a camera) according to an exemplary embodiment. The camera control module can be a stand alone hardware control module. This module can include functions to read images from the camera and perform at least two types of object detection: barcode reading and gaze detection. The barcode reading function can be used to facilitate user login and/or patient entry. If the device is used in an environment where patient barcodes are available and an EHR system is connected, the barcode scan will make the connection to the EHR database and modify or create the patient record as needed. The gaze detection portion of the camera module will determine the position and direction the patient's eyes are looking. If the software determines that the patient is gazing correctly at the fixation target and the eyes are the correct distance from the device, this module can send a signal over the IPC messaging system to commence a scan. This module can be written in, for example, Python and can use the OpenCV image processing library. The camera module also also dump captured images into a shared memory space to allow the GUI to display the camera images during a barcode scan or immediately prior to testing. The camera module will also be configured to run as a system service.

Signal Processing

The signal processing module can also be a standalone hardware module. This module can communicate with a high speed (Analog-Digital Converter) ADC to read data from the device's optical sensors. The ADC can have a minimum digital conversion width of 12 bits and an SNR of >50 db. The ADC shall also have less than 1% sampling jitter and a minimum 200 ksps sampling rate. The Sampling reference voltage not to exceed 3.0V. The preferred ADC specifications would be a sampling rate of >200 ksps and 16 bit resolution across 2V reference. The ADC will interface with an FPGA containing enough memory to store all 10 trials that make up one test. The FPGA will act as a FIFO buffer to the embedded Linux device over SPI. The embedded Linux device requires 8 bit SPI words per enable. The SPI interface can run at 8 MHz to minimize data transfer times. After reading and stitching all the data from the ADC, the signal processing module will process the data to obtain test results. Data collected with the shutter closed will act as a background measurement. After performing a Fourier transform on the data, the background frequencies will be subtracted from the test data. The remains peaks at frequencies of interest will be evaluated to determine if fixation is present. This result, along with other specified metrics will then be saved to a patient record on the device as YAML file and the data service will be notified that a new patient record is available. This patient record will be temporary and will be destroyed after the current user logs out. The data service will ensure the correct long term storage solution for the patient record.

The data service ensures the correct transmission or long term management of the on board patient records. The patient records can be encrypted using (TBR 128 bit)-AES encryption when stored locally. The record can then be transferred electronically to an EHR or other external data service over an SSL secured connection. If so configured, a web server or FTP server may be available on the device for local access and transfer. These two services will also ensure an SSL connection as well. A USB device may also be used to transfer the data off of the device.

It will be appreciated by those skilled in the art that changes could be made to the embodiments described above without departing from the broad inventive concept thereof. For example, the steps or order of operation of one of the above-described methods could be rearranged or occur in a different series, as understood by those skilled in the art. It is understood, therefore, that this disclosure is not limited to the particular embodiments disclosed, but it is intended to cover modifications within the spirit and scope of the present disclosure as defined by the appended claims.

The invention claimed is:

1. An apparatus for ophthalmic neural scanning, the apparatus comprising:
a projection apparatus configured to project a projected image onto one or more retinas of one or more eyes of a subject;
one or more photodetectors disposed conjugate to the one or more retinas, wherein the one or more photodetectors are configured to capture a reflected image reflected from the one or more retinas in response to the projected image, the reflected image including information indicating fixation of the one or more eyes; and
an image capture device disposed conjugate to one or more corneas of the one or more eyes of the subject and configured to capture a diagnostic image including one or more pupils of the one or more eyes when the one or more pupils are illuminated by retroreflected light from the one or more retinas in response to the projected image.

2. The apparatus of claim 1, wherein the projected image comprises a ring image and wherein the projection apparatus comprises:
a light source configured to project light; and
a concave toroidal mirror configured to reflect the light projected from the light source into the ring image.

3. The apparatus of claim 1, wherein the projected image comprises a ring image and wherein the projection apparatus comprises:
a light source configured to project light through an axicon lens to thereby generate a circular light projection; and
a toroidal lens configured to focus the circular light projection into the ring image.

4. The apparatus of claim 1, wherein the projected image comprises a ring image and wherein the projection apparatus comprises:
a light source configured to project light onto a first concave mirror; and
the first concave mirror being configured to rotate about a rotation axis and re-image the light projected from the light source onto a second concave mirror to create the appearance of the ring image on the second concave mirror.

5. The apparatus of claim 1, wherein the projection apparatus comprises an image projector configured to project a stimulus, the stimulus comprising a grid of double lines or a plurality of concentric circles.

6. The apparatus of claim 1, further comprising:
a second projection apparatus configured to project a fixation target that is configured to appear to the subject to be centered within the projected image.

7. The apparatus of claim 6, wherein the second projection apparatus comprises:
a display configured to generate the fixation target; and
a reflector configured to reflect the fixation target onto a window of a housing that surrounds the projection apparatus, the one or more photodetectors, and the second projection apparatus.

8. The apparatus of claim 1, wherein the image capture device is aligned with an optical axis of the projected image, the ophthalmic neural scanner apparatus further comprising:
a toric mirror aligned with the optical axis and configured to reflect the projected image onto the one or more retinas and re-reflect the reflected image onto a propagation path to the one or more photodetectors, wherein the toric mirror comprises an aperture configured to allow retroreflected light to pass through to the image capture device.

9. The apparatus of claim 1, further comprising:
one or more processors; and
one or more memories operatively coupled to at least one of the one or more processors and having instructions stored thereon that, when executed by at least one of the one or more processors, cause at least one of the one or more processors to:
analyze the diagnostic image to generate diagnostic metadata pertaining to a usage of the ophthalmic neural scanner apparatus.

10. The apparatus of claim 9, wherein at least one of the one or more memories has further instructions stored thereon that, when executed by at least one of the one or more processors, cause at least one of the one or more processors to:

transmit the diagnostic metadata to a display device integrated with the ophthalmic neural scanner apparatus.

11. The apparatus of claim 9, wherein the diagnostic metadata comprises metadata pertaining to the one or more pupils and wherein at least one of the one or more memories has further instructions stored thereon that, when executed by at least one of the one or more processors, cause at least one of the one or more processors to:
    determine whether the one or more pupils are present in the diagnostic image based at least in part on the diagnostic metadata;
    determine whether a location of the one or more pupils is within a boundary of a target location required to initiate a scan based at least in part on the diagnostic metadata; and
    transmit a command to the one or more photodetectors to capture the reflected image based at least in part on a determination that the one or more pupils are present in the diagnostic image and a determination that the location of the one or more pupils is within the boundary of the target location required to initiate a scan.

12. The apparatus of claim 9, wherein the diagnostic metadata comprises information relating to one or more of:
    a measurement of background light;
    a presence of the one or more pupils;
    a location of the one or more pupils;
    a size of the one or more pupils; or
    a blink rate of the subject.

13. The apparatus of claim 9, wherein at least one of the one or more memories has further instructions stored thereon that, when executed by at least one of the one or more processors, cause at least one of the one or more processors to:
    determine one or more fixation measurements of the one or more eyes based at least in part on the projected image and the reflected image.

14. The apparatus of claim 9, wherein at least one of the one or more memories has further instructions stored thereon that, when executed by at least one of the one or more processors, cause at least one of the one or more processors to:
    identify one or more possible health conditions of the subject based at least in part on one or more of: the one or more fixation measurements or the diagnostic metadata; and
    transmit information relating to the one or more possible health conditions.

15. The apparatus of claim 14, wherein the one or more possible health conditions comprise one or more of: brain trauma, impeded brain function, brain injury, strabismus, ocular motor apraxia, or amblyopia.

16. A method for ophthalmic neural scanning, the method comprising:
    projecting, by a projection apparatus, a projected image onto one or more retinas of one or more eyes of a subject;
    capturing, by one or more photodetectors disposed conjugate to the one or more retinas, a reflected image reflected from the one or more retinas in response to the projected image, the reflected image including information indicating fixation of the one or more eyes; and
    capturing, by an image capture device disposed conjugate to one or more corneas of the one or more eyes of the subject, a diagnostic image including one or more pupils of the one or more eyes when the one or more pupils are illuminated by light retroreflected from the one or more retinas in response to the projected image.

17. The method of claim 16, wherein the projected image comprises a ring image and wherein projecting, by a projection apparatus, a projected image onto one or more retinas of one or more eyes of a subject comprises:
    projecting, by a light source, light onto a concave toroidal mirror; and
    reflecting, by the concave toroidal mirror, the light projected from the light source into the ring image.

18. The method of claim 16, wherein the projected image comprises a ring image and wherein projecting, by a projection apparatus, a projected image onto one or more retinas of one or more eyes of a subject comprises:
    projecting, by a light source, light through an axicon lens to thereby generate a circular light projection; and
    focusing, by a toroidal lens, the circular light projection into the ring image.

19. The method of claim 16, wherein the projected image comprises a ring image and wherein projecting, by a projection apparatus, a projected image onto one or more retinas of one or more eyes of a subject comprises:
    projecting, by a light source, light onto a first concave mirror, the first concave mirror being configured to rotate about a rotation axis; and
    re-imaging, by the first concave mirror, the light projected from the light source onto a second concave mirror to create the appearance of the ring image on the second concave mirror.

20. The method of claim 16, wherein the projection apparatus comprises an image projector and wherein projecting, by a projection apparatus, a projected image onto one or more retinas of one or more eyes of a subject comprises:
    projecting, by the image projector, a stimulus comprising either a grid of double lines or a plurality of concentric circles.

21. The method of claim 16, further comprising:
    projecting, by a second projection apparatus, a fixation target that is configured to appear to the subject to be centered within the projected image.

22. The method of claim 16, wherein projecting, by a second projection apparatus, a fixation target that is configured to appear to the subject to be centered within the projected image comprises:
    generating, by a display, the fixation target; and
    reflecting, by a reflector, the fixation target onto a window of a housing that surrounds the projection apparatus, the one or more photodetectors, and the second projection apparatus.

23. The method of claim 16, wherein the image capture device is aligned with an optical axis of the projected image and further comprising:
    reflecting, by a toric mirror aligned with the optical axis, the projected image onto the one or more retinas; and
    re-reflecting, by the toric mirror aligned with the optical axis, the reflected image onto a propagation path to the one or more photodetectors;
    wherein the toric mirror comprises an aperture configured to allow retroreflected light to pass through to the image capture device.

24. The method of claim 16, further comprising:
    analyzing, by at least one of one or more computing devices, the diagnostic image to generate diagnostic metadata pertaining to a usage of the ophthalmic neural scanner apparatus.

25. The method of claim 24, further comprising:
transmitting, by at least one of the one or more computing devices, the diagnostic metadata to a display device.

26. The method of claim 24, wherein the diagnostic metadata comprises metadata pertaining to the one or more pupils and further comprising:
determining, by at least one of the one or more computing devices, whether the one or more pupils are present in the diagnostic image based at least in part on the diagnostic metadata;
determining, by at least one of the one or more computing devices, whether a location of the one or more pupils is within a boundary of a target location required to initiate a scan based at least in part on the diagnostic metadata; and
transmitting, by at least one of the one or more computing devices, a command to the one or more photodetectors to capture the reflected image based at least in part on a determination that the one or more pupils are present in the diagnostic image and a determination that the location of the one or more pupils is within the boundary of the target location required to initiate a scan.

27. The method of claim 24, wherein the diagnostic metadata comprises information relating to one or more of:
a measurement of background light;
a presence of the one or more pupils;
a location of the one or more pupils;
a size of the one or more pupils; or
a blink rate of the subject.

28. The method of claim 24, further comprising:
determining, by at least one of the one or more computing devices, one or more fixation measurements of the one or more eyes based at least in part on the projected image and the reflected image.

29. The method of claim 28, further comprising:
identifying, by at least one of the one or more computing devices, one or more possible health conditions of the subject based at least in part on one or more of: the one or more fixation measurements or the diagnostic metadata; and
transmitting, by at least one of the one or more computing devices, information relating to the one or more possible health conditions.

30. The method of claim 29, wherein the one or more possible health conditions comprise one or more of: brain trauma, impeded brain function, brain injury, strabismus, ocular motor apraxia, or amblyopia.

* * * * *